United States Patent [19]

Sunkara et al.

[11] Patent Number: 4,952,585

[45] Date of Patent: Aug. 28, 1990

[54] CASTANOSPERMINE ESTERS IN THE INHIBITION OF TUMOR METASTASIS

[75] Inventors: Sai P. Sunkara; Paul S. Liu, both of Cincinnati, Ohio

[73] Assignee: Merrell Dow Pharmaceuticals Inc., Cincinnati, Ohio

[21] Appl. No.: 284,510

[22] Filed: Dec. 15, 1988

[51] Int. Cl.$^5$ ............................................ A61K 31/44
[52] U.S. Cl. .................................................... 514/299
[58] Field of Search ......................................... 514/299

[56] References Cited

U.S. PATENT DOCUMENTS 4,792,558  12/1988  Sunkara et al. ...................... 514/299

OTHER PUBLICATIONS

Tohru Kino et al., *The Journal of Antibiotics*, 38, 936–940, (1985).

Martin J. Humphries et al., *Cancer Research*, 46, 5215–5222, (1986).

*Primary Examiner*—Jerome D. Goldberg
*Attorney, Agent, or Firm*—John J. Kolano

[57] ABSTRACT

A method for the inhibition of tumor metastases is described herein. The method makes use of the administration of certain castanospermine esters or their pharmaceutically acceptable salts.

10 Claims, No Drawings

CASTANOSPERMINE ESTERS IN THE INHIBITION OF TUMOR METASTASIS

BACKGROUND OF THE INVENTION

The spread of cancer cells from a primary tumor site to distant organs is known as metastasis. Metastasis has been considered one of the most intriguing aspects of the pathogenesis of cancer. This is certainly true to the extent that cancer metastasis is responsible for most therapeutic failures when the disease is treated, as patients succumb to the multiple tumor growth. The extent to which metastasis occurs varies with the individual type of tumor. Melanoma, breast cancer, lung cancer and prostate cancer are particularly prone to metastasize.

When metastasis takes place, the secondary tumors can form at a variety of sites in the body, with one of the more common sites for metastasis being the lung.

Thus, inhibition of tumor metastasis to any extent would be beneficial and this would be true regardless of whether the agent involved in the inhibition had any effect on the primary tumor. Of course, if the agent also inhibited the primary tumor, this would be an additional advantage for the agent.

Humphries et al., *Cancer Research,* 46, 5215 (1986) describes the inhibition of experimental metastasis by castanospermine in mice. In addition, U.S. patent application Ser. No. 55,589, filed May 29, 1987 (U.S. Pat. No. 4,792,558) also describes the use of castanospermine in the inhibition of metastasis.

SUMMARY OF THE INVENTION

It has now been found that certain esters of castanospermine are also useful in the inhibition of tumor metastasis. More particularly, it has been found that certain monoesters of castanospermine or their pharmaceutically acceptable salts are useful in the inhibition of tumor metastasis. Castanospermine can also be named in other ways as follows: (1S,6S,7R,8R,8aR)-1,6,7,8-tetrahydroxyindolizidine or [1S-(1α,6β,7α,8β,8aβ)]-octahydro-1,6,7,8-indolizinetetrol.

More specifically, the present invention relates to a method for inhibiting the formation of tumor metastases only comprising the administration of an amount, which is safe and sufficient to inhibit the formation of tumor metastases, of a castanospermine ester of the formula:

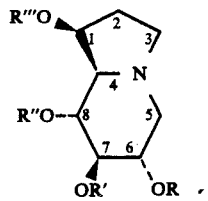

wherein R, R', R" and R'" are selected so that three of them are hydrogen and the fourth is alkanoyl of 1 to 18 carbon atoms, benzoyl, ($C_{1-4}$ alkyl)benzoyl, ($C_{1-4}$ alkyl)$_2$benzoyl, ($C_{1-4}$ alkoxy)benzoyl, halobenzoyl, dichlorobenzoyl, trichlorobenzoyl, trifluoromethylbenzoyl, ($C_{1-4}$ alkylsulfonyl)benzoyl, ($C_{1-4}$ alkylmercapto)benzoyl, cyanobenzoyl, dimethylaminobenzoyl, thiophenecarbonyl or furancarbonyl, or a pharmaceutically acceptable salt thereof, to a patient having melanoma, breast cancer, lung cancer or prostate cancer.

The pharmaceutically acceptable salts of the castanospermine esters can be exemplified by those with inorganic acids such as hydrochloric acid, hydrobromic acid, sulfuric acid and phosphoric acid; and with organic acids such as acetic acid, methanesulfonic acid and p-toluenesulfonic acid. In the various alkyl-, alkoxy-, alkylsulfonyl- and alkylmercapto- substituted benzoyl groups referred to above, the alkyl portion contains 1 to 4 carbon atoms and can be exemplified by methyl, ethyl, propyl and butyl. In the halobenzoyl group referred to above, the halogen can be fluorine, chlorine, bromine or iodine. In the various substituted benzoyl groups referred to above, the substituent can't be located at the 2-, 3- or 4-positions. Similarly, where there is more than one substituent, they can be located at any of the various positions available on the benzene ring.

The alkanoyl groups referred to above can be straight- or branched-chain and can be exemplified by formyl, acetyl, propionyl, butyryl, isobutyryl and hexanoyl.

A preferred embodiment of the present invention relates to the method of the present invention wherein, in the general formula as shown above, R, R', R" and R'" are selected so that three of them are hydrogen and the fourth is acetyl, propionyl, benzoyl, methylbenzoyl or furancarbonyl.

The esters used in the present invention are prepared by the reaction of castanospermine with an appropriate acid chloride or anhydride in an inert solvent. The halide can be a chloride or bromide and the anhydride includes mixed anhydrides. The relative amount of the acid halide or anhydride used, the relative amount of solvent, the temperature and the reaction time are all controlled so as to minimize the number of hydroxy groups that will be acylated. Thus, only a limited excess of the acid derivative is used, which means up to about a three-fold excess of the acylating agent. Use of a solvent in relatively large amounts, serves to dilute the reactants and hold down the amount of higher acylated products that form. The solvent used is preferably one that will dissolve the reactants used without reacting with them. It is further preferable to carry out the reaction in the presence of a tertiary amine which will react with and remove any acid formed during the course of the reaction. The tertiary amine can be added to the mixture or it can itself be used in excess and serve as the solvent. Pyridine is a preferred solvent in this regard. As indicated above, the time and the temperature are likewise controlled to limit the extent of acylation that takes place. Preferably, the reaction is carried out with cooling in an ice-bath for a period of about 16 hours to give the desired monoesters. The reaction can actually be carried out at higher temperatures and, in fact, heating can be used as long as the various factors involved are properly controlled. The fact of the matter is, when the reaction is carried out as described, the final reaction mixture will still contain a considerable amount of unreacted castanospermine. This unreacted material can be recovered from the reaction mixture and recycled in subsequent reactions and thus increase the overall amount of castanospermine converted to ester. This recycling is particularly important in the present situation where the reaction is carried out under conditions which would favor the isolation of monoesters.

The procedures as described above will generally give the 6- or 7-monoesters. The 1- or 8-isomers can be obtained by appropriate use of blocking groups. Thus, for example, under appropriate conditions, castanospermine can be reacted with 2-(dibromomethyl)benzoyl chloride to give the 6,7-diester. This diester is then reacted with an appropriate acid halide or anhydride to give the corresponding 1- or 8-ester. The two protecting groups are then readily removed, without affecting the 1- or 8-ester, by conversion of the two dibromomethyl groups to formyl (using silver perchlorate and 2,4,6-collidine in aqueous acetone) followed by selective hydrolysis of the resultant formylbenzoic esters using morpholine and hydroxide ion.

The experiments below demonstrates the ability of castanospermine esters or their compositions to inhibit metastasis of tumor cells and, particularly, metastasis of tumor cells to lungs. The lungs provide a convenient organ for the study of metastasis in the animal body.

A single suspension of $B_{16}F_{10}$ melanoma cells was prepared from a 14 day old maintenance tumor excised from a C57 male mouse. The tumor was minced and trypsinized followed by dissociation of the cells in minimal essential medium (MEM) with fetal calf serum (FCS) by repeated pipetting. The preparation was passed through a sterile gauze pad, centrifuged, and the cell pellet washed in minimal essential medium without fetal calf serum. A trypan blue wet mount was made to determine the percent of viable cells.

The cells were then plated in 100 mm petri dishes at $0.5 \times 10^6$ viable cells/10 ml minimal essential medium with fetal calf serum and incubated at 37° C. for 24 to 48 hours. After incubation, the medium was aspirated and 10 ml of the test compounds at the concentrations of 1 μg or 10 μg/ml MEM with FCS was added. After 24 hours incubation, the medium was aspirated and 10 ml of fresh test compound-medium preparation was added.

Test compounds were dissolved in water or dimethyl sulfoxide and then diluted to the testing concentrations with medium. Control plates receive only medium and/or medium containing dimethyl sulfoxide.

After a total of 48 hours incubation, the testing medium was aspirated, the cells trypsinized and suspended in MEM with FCS. The cells were washed in MEM without FCS and resuspended at the concentration of $10 \times 10^5$ cells/ml of MEM without FCS.

C57 male mice weighing 20–25 grams (Charles River) were inoculated intravenously via the tail vein with $2 \times 10^5$ cells per 0.2 ml MEM without FCS/mouse. Fifteen days after inoculation, the animals were sacrificed by carbon dioxide inhalation and the lungs were removed and placed in formalin solution. The number of pulmonary foci per animal lung was counted (after separating the lobes) under a lighted dissecting lens.

Data can be expressed as the mean number of foci±S.E. per control and treatment groups. Treatment group data is also expressed as a percent of control and percent of inhibition (100% minus % of control). When the procedure described above was carried out on the castanospermine esters listed below, the per cent inhibition of metastases observed [at the dose, in micrograms per milliliter (μg/ml), given in parentheses] was as follows:

[1S-(1α,6β,7α,8β,8aβ)]-Octahydro-1,6,7,8-indolizinetetrol 6-benzoate, 35% (1).
[1S-(1α,6β,7α,8β,8aβ)]-Octahydro-1,6,7,8-indolizinetetrol 7-benzoate, 23% (1).
[1S-(1α,6β,7α,8β,8aβ)]-Octahydro-1,6,7,8-indolizinetetrol 6-(4-methoxybenzoate), 19% (1).
[1S-(1α,6β,7α,8β,8aβ)]-Octahydro-1,6,7,8-indolizinetetrol 6-(4-methylbenzoate), 75% (10).
[1S-(1α,6β,7α,8β,8aβ)]-Octahydro-1,6,7,8-indolizinetetrol 7-(4-methylbenzoate), 65% (1).
[1S-(1α,6β,7α,8β,8aβ)]-Octahydro-1,6,7,8-indolizinetetrol 6-(3-methylbenzoate), 78% (1).
[1S-(1α,6β,7α,8β,8aβ)]-Octahydro-1,6,7,8-indolizinetetrol 6-(2-methylbenzoate), 71% (10).
[1S-(1α,6β,7α,8β,8aβ)]-Octahydro-1,6,7,8-indolizinetetrol 6-(2-furancarboxylate), 51% (1).
[1S-(1α,6β,7α,8β,8aβ)]-Octahydro-1,6,7,8-indolizinetetrol 6-acetate, >50% (1).
[1S-(1α,6β,7α,8β,8aβ)]-Octahydro-1,6,7,8-indolizinetetrol 7-propionate, 36% (1).
[1S-(1α,6β,7α,8β,8aβ)]-Octahydro-1,6,7,8-indolizinetetrol 6-butanoate, 13% (10).

In another experiment, $1 \times 10^5$ viable B16 melanoma F10 line cells were injected i.v. through the tail vein of C57/BL mice. Test compound was then administered at 100 mg/kg, i.p. daily from day 1–15. At the end of 15 days, the animals were sacrificed and the number of metastatic foci in the lungs were quantitated and compared to controls run simultaneously. The percent inhibition of metastasis observed is summarized in the table below.

| TEST COMPOUND | % INHIBITION |
| --- | --- |
| [1S-(1α,6β,7α,8β,8aβ)]-Octahydro-1,6,7,8-indolizinetetrol 6-benzoate | 66 |
| [1S-(1α,6β,7α,8β,8aβ)]-Octahydro-1,6,7,8-indolizinetetrol 6-(4-methylbenzoate) | 71 |
| [1S-(1α,6β,7α,8β,8aβ)]-Octahydro-1,6,7,8-indolizinetetrol 6-(2-furancarboxylate) | 40 |

From the above results, it can be seen that the esters of castanospermine significantly inhibited metastasis in the animals.

The method of treatment by inhibition of metastasis disclosed and claimed herein may be used alone or in combination as part of a treatment regimen for an animal or human patient having a cancer that is prone to metastasis, particularly, melanoma, breast cancer, lung cancer and prostate cancer. The treatment to inhibit the formation of metastases is best administered as soon after the detection of the cancer as possible. By utilizing the treatment regimen in patients at an early stage, the treating physician maximizes the chances that significant metastasis has not yet occurred. This maximizes chances for successful treatment. In such a regimen, the castanospermine ester or its salts may, and generally will, be administered in combination with another form of therapy which controls the primary tumor itself. The other therapy in such a combination can include, but is not limited to, radiation therapy or the administration of compatible antitumor or antineoplastic agents. Examples of such antineoplastic agents include melphalan, lomustine capsules, cyclophosphamide, fluorouracil and also ornithine decarboxylase inhibitors such as difluoromethylornithine (DFMO), 6-heptyne-2,5-diamine and (E)-2,5-diamino-2-(fluoromethyl)-3-pentenoic acid methyl ester dihydrochloride. The treatment described in the present application may also be used conjointly with (i.e., either preceding or subsequent to) a surgical procedure to remove the primary tumorous material from the body. Frequently, surgical procedures to remove tumorous material from the body are avoided because of the fear that metastasis will occur as a result of the physical dissemination of the tumor tissues. However, if the castanospermine ester or its salts are administered to the patient prior to the surgical procedure, then the risk of metastasis which may result from surgery can be reduced and surgery would be a more attractive treatment option.

Within the scope of sound medical judgment, the dosage of castanospermine or its salts and the method of administration used in the present invention will vary with the severity and nature of the particular condition being treated, the duration of treatment, the adjunct therapy used, the age and physical condition of the patient, and like factors within the specific knowledge and expertise of the attending physician. However, single dosages can typically range from 0.1 to 2000 milligrams per kilogram of body weight, preferably 1 to 200 milligrams per kilogram (unless otherwise specified, the unit designated "mg/kg", as used herein, refers to milligrams per kilogram of body weight). Up to four doses per day can be used routinely, but this can be varied according to the needs of the patient, consistent with a sound benefit/risk ratio. Variation in patient response may be expected but the higher dosages within the ranges indicated are usually required in the case of oral administration while the lower dosages indicated would apply for intravenous administration.

For purposes of oral administration, the castanospermine ester or its salts can be formulated in the form of capsules, tablets or granules while for intravenous administration, the active material can be formulated in an appropriate solution. In any case, the active compound is mixed with an appropriate pharmaceutical carrier.

As used herein, the term "pharmaceutical carrier" denotes a solid or liquid filler, diluent or encapsulating substance. Some examples of the substances which can serve as pharmaceutical carriers are sugars, such as lactose, glucose and sucrose; starches, such as corn starch and potato starch; cellulose and its derivatives, such as sodium carboxymethyl cellulose, ethyl cellulose, cellulose acetate; powdered tragacanth; malt; gelatin; talc; stearic acid; magnesium stearate; calcium sulfate; vegetable oils, such as peanut oil, cottonseed oil, sesame oil, olive oil, corn oil and oil of theobroma; polyols, such as propylene glycol, glycerin, sorbitol, mannitol, and polyethylene glycol; agar; alginic acid; pyrogen-free water; isotonic saline; and phosphate buffer solutions, as well as non-toxic compatible substances used in pharmaceutical formulations. Wetting agents and lubricants, such as sodium lauryl sulfate, as well as coloring agents, flavoring agents, tableting agents, and preservatives, can also be present. Tableting or any other formulation is done using conventional techniques. Additional information about suitable pharmaceutical carriers and formulation techniques are found in standard texts, such as *Remington's Pharmaceutical Sciences*, Mack Publishing Company, Easton, Pa.

The pharmaceutical carrier employed in conjunction with the castanospermine ester or its salt is used at a concentration sufficient to provide a practical size to dosage relationship. Preferably, the pharmaceutical carrier comprises from about 0.1% to 99% by weight of the total composition.

The following examples are further presented to illustrate the preparation of the compounds used in the present invention.

EXAMPLE 1

A slurry of 4.0 g of castanospermine in 140 ml of pyridine was stirred at room temperature for 30 minutes until essentially all of the solids had dissolved. The solution was cooled to 0° C. in an ice/water bath, and a solution of 5.85 ml of benzoyl chloride in 15 ml of pyridine was added dropwise over 15 minutes under nitrogen. After the addition, the reaction was stirred at 8° C. overnight.

The reaction mixture was partitioned between 225 ml methylene chloride and 300 ml water. The organic layer was separated and the aqueous layer extracted with two 225-ml portions of methylene chloride. The combined organic layers were washed successively with 150 ml of 0.5N hydrochloric acid, saturated sodium carbonate, water and saturated sodium chloride solutions, and then dried over sodium sulfate. Evaporation of solvents under reduced pressure gave 2.9 g of a tan glassy residue.

This material was slurried in chloroform and a white precipitate formed. These solids were isolated to afford 910 mg of a white powder. Thin layer chromatography (85:15, ethyl acetate:methanol) analysis showed the material to be composed of two components (Rf 0.33 and Rf 0.26). The solid mixture was slurried in 45 ml of 4:1 ethyl acetate:methanol and filtered. The residue was dried in vacuo to provide 350 mg of [1S-($1\alpha,6\beta,7\alpha,8\beta,8a\beta$)]-octahydro-1,6,7,8-indolizinetetrol 6-benzoate as a white powdery solid melting at about 233°–236° C., with decomposition. This corresponded to the less polar component of the mixture. NMR (DMSO-$d_6$) δ 1.5–2.2 (m, 5H), 2.9–3.6 (m, 4H), 4.1 (m, 1H, $C_1$-H), 4.3 (d, 1H, —OH) 4.7 (d, 1H, —OH), 4.8 (sextet, 1H, $C_6$-H), 5.1 (d, 1H, —OH), 7.6–8.1 (m, 5H, aryl). MS (CI—$CH_4$) 294 (MH$^+$), 276 (MH$^+$—$H_2O$), 172 (MH$^+$—$PhCO_2H$).

The filtrate from above was condensed and fractionated by preparative thin layer chromatography (silica gel, 80:20, ethyl acetate:methanol) to provide 120 mg of the more polar component, [1S-($1\alpha,6\beta,7\alpha,8\beta,8a\beta$)]-octahydro-1,6,7,8-indolizinetetrol 7-benzoate as a white powdery solid melting at about 200°–202° C. NMR (DMSO-$d_6$+$D_2O$) 1.5–2.2 (m, 5H), 2.9–3.1 (m, 2H), 3.6–3.8 (m, 2H), 4.1 (m, 1H, $C_1$—H), 4.8 (t, 1H, $C_7$—H), 7.4–8.1 (m, 5H, aryl). MS (CI—$CH_4$) 294 (MH$^+$), 276 (MH$^+$-$H_2O$), 172 (MH$^+$-$PhCO_2H$).

EXAMPLE 2

Castanospermine (1.89 g) was added to a stirred solution of 10 ml of pyridine and cooled to 0° C. in an ice bath. Benzoyl chloride, 3.0 g, was added dropwise to the mixture and the resulting suspension was kept at 0°–4° C. for 7 days. Water, 10 ml, was added and the mixture was evaporated to dryness in vacuo. The resulting residue was redissolved in 1:1 water:ethyl acetate (100 ml) and the phases were separated. The aqueous layer was extracted again with 100 ml of ethyl acetate. The organic extracts were combined and concentrated to a syrup which was shown to be a mixture of two major components by thin layer chromatography (1:1 ethyl acetate:hexane, silica gel, Rf=0.42 and Rf=0.11). The mixture was separated by preparative high pressure liquid chromatography (silica gel, 1:1 ethyl acetate:hexane) to provide 1.9 g (48%) of the more polar component, [1S-($1\alpha,6\beta,7\alpha,8\beta,8a\beta$)]-octahydro-1,6,7,8-indolizinetetrol 6,7-dibenzoate as a dry foam melting at about 79°–81° C. NMR (DMSO-$d_6$/$D_2O$) δ 1.5–2.3 (m, 5H), 3.0–3.4 (m, 2H), 3.9 (t, 1H), 4.2 (m, 1H, $C_1$—H), 5.15 (m, 1H, $C_6$—H), 5.3 (t, 1H, $C_7$—H), 7.4–8.0 (m, 10H, aryl). MS (FAB—Xe) 398 (MH$^+$), 380 (MH$^+$—$H_2O$), 276 (MH$^+$—$PhCO_2H$).

EXAMPLE 3

When the procedure of Example 1 was repeated using castanospermine and the appropriate acid chloride, the following compounds were obtained:

[1S-(1α,6β,7α,8β,8aβ)]-octahydro-1,6,7,8-indolizinetetrol 6-(4-fluorobenzoate) melting at about 216°–218° C.

[1S-(1α,6β,7α,8β,8aβ)]-octahydro-1,6,7,8-indolizinetetrol 7-(4-fluorobenzoate) melting at about 190°–193° C.

[1S-(1α,6β,7α,8β,8aβ)]-octahydro-1,6,7,8-indolizinetetrol 7-(2,4-dichlorobenzoate) melting at about 179°–181° C.

[1S-(1α,6β,7α,8β,8aβ)]-octahydro-1,6,7,8-indolizinetetrol 6-(4-bromobenzoate) melting at about 234°–235° C.

[1S-(1α,6β,7α,8β,8aβ)]-octahydro-1,6,7,8-indolizinetetrol 7-(4-bromobenzoate) melting at about 199°–202° C.

[1S-(1α,6β,7α,8β,8aβ)]-octahydro-1,6,7,8-indolizinetetrol 6-(4-methoxybenzoate) melting at about 221°–224° C.

EXAMPLE 4

To a suspension of 3 g of castanospermine in 30 ml of pyridine at 0° C. was added dropwise a solution of 3 g of 4-methylbenzoyl chloride. After the addition, the mixture was allowed to warm to room temperature and then heated at 55° C. for 24 hours. The reaction mixture was diluted with 10 ml of water and evaporated to dryness in vacuo. The resulting residue was stirred in 150 ml of a 1:2 mixture of water: methylene chloride. The insoluble material was separated by filtration to provide an amorphous off-white solid which was dissolved in 60 ml of hot methanol, treated with 0.5 g of activated charcoal and filtered. The colorless filtrate was cooled to give colorless crystals of [1S-(1α,6β,7α,8β,8aβ)]-octahydro-1,6,7,8-indolizinetetrol 6-(4-methylbenzoate) melting at about 255°–258° C. with decomposition (580 mg, 12% yield).

The two-phase water/methylene chloride mixture obtained above was evaporated to dryness and the residue was dissolved in 50 ml of a 1:2 mixture of methanol:ethyl acetate. The solution was fractionated by preparative high pressure liquid chromatography (silica gel, 9:1 ethyl acetate: methanol) and fractions containing the more polar component (i.e., more polar than the 6-ester obtained in the preceding paragraph) were collected and evaporated in vacuo to provide a colorless solid which was [1S-(1α,6β,7α,8β,8aβ)]-octahydro-1,6,7,8-indolizinetetrol 7-(4-methylbenzoate) melting at about 220°–223° C. with decomposition (210 mg, 4% yield).

EXAMPLE 5

When the procedure of Example 4 was repeated using castanospermine and the appropriate acid chloride, the following esters were obtained:

6-(2-Methylbenzoate) melting at about 213°–215° C.

6-(3-Methylbenzoate) melting at about 212° C. with decomposition.

7-(3-Methylbenzoate).

6-(3-Trifluoromethylbenzoate).

6-(4-Methylsulfonylbenzoate).

6-(4-Methylmercaptobenzoate).

6-(3-Cyanobenzoate).

6-(4-Dimethylaminobenzoate).

6-(3,4,5-Trichlorobenzoate).

6-(2,4-Dimethylbenzoate).

6-(2-Thiophenecarboxylate) melting at about 214°–215° C.

6-(2-Furancarboxylate) melting at about 209°–212° C.

EXAMPLE 6

To a stirred suspension of 1.5 g of castanospermine in 15 ml of pyridine cooled at 0° C. in an ice-bath was added dropwise 1.0 g of butyryl chloride. The mixture was stirred at room temperature for 3 days and added to a 1:1 mixture of water:methylene chloride (400 ml). After partitioning, the aqueous phase was concentrated in vacuo to provide an oily residue which was fractionated by radial thin layer chromatography (silica gel, 2 mm thickness plate, 2:8 methanol: chloroform) to provide 68 mg of [1S-(1α,6β,7α,8β,8aβ)]-octahydro-1,6,7,8-indolizinetetrol 6-butanoate, homogeneous by thin layer chromatography (silica gel, 2:8 methanol: chloroform, Rf=0.5). Recrystallization of the product from 5:95 isopropanol:hexane gave a colorless solid melting at 113°–114° C. NMR (CDCl$_3$) δ 3.5–3.8 (2t, 2H, C$_7$-H and C$_8$-H), 4.4 (m, 1H, C$_1$-H), 4.95 (m, 1H, C$_6$-H). MS (CI—CH$_4$) 260 (MH+), 242 (MH+—H$_2$O), 172 (MH+—C$_3$H$_7$CO$_2$H).

Similarly, when the above procedure was repeated using acetyl chloride or propionyl chloride, the following monoesters were obtained:

[1S-(1α,6β,7α,8β,8aβ)]-octahydro-1,6,7,8-indolizinetetrol 6-acetate melting at about 188°–189° C.

[1S-(1α,6β,7α,8β,8aβ)]-octahydro-1,6,7,8-indolizinetetrol 7-propionate melting at about 153°–155° C.

What is claimed is:

1. A method for inhibiting the formation of tumor metastases only which comprises administering an amount, which is safe and sufficient to inhibit the formation of tumor metastases, of a castanospermine ester of the formula:

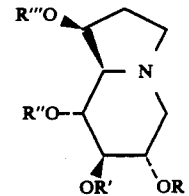

wherein R, R', R" and R''' are selected so that three of them are hydrogen and the fourth is alkanoyl of 1 to 18 carbon atoms, benzoyl, (C$_{1-4}$ alkyl)benzoyl, (C$_{1-4}$ alkyl)$_2$benzoyl, (C$_{1-4}$ alkoxy)benzoyl, halobenzoyl, dichlorobenzoyl, trichlorobenzoyl, trifluoromethylbenzoyl, (C$_{1-4}$ alkylsulfonyl)benzoyl, (C$_{1-4}$ alkylmercapto)benzoyl, cyanobenzoyl, dimethylaminobenzoyl, thiophenecarbonyl or furancarbonyl, or a pharmaceutically acceptable salt thereof, to a patient having melanoma, breast cancer, lung cancer or prostate cancer.

2. A method according to claim 1 for inhibiting the formation of tumor metastases which comprises administering an amount, which is safe and sufficient to inhibit the formation of tumor metastases, of a castanospermine ester of the formula:

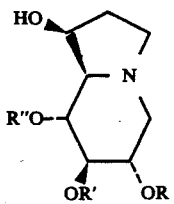

wherein R, R' and R" are selected so that two of them are hydrogen and the third is alkanoyl of 1 to 10 carbon atoms, benzoyl, (C$_{1-4}$ alkyl)benzoyl, (C$_{1-4}$ alkyl)$_2$benzoyl, (C$_{1-4}$ alkoxy)benzoyl, halobenzoyl, dichlorobenzoyl, trichlorobenzoyl, trifluoromethylbenzoyl, (C$_{1-4}$ alkylsulfonyl)benzoyl, (C$_{1-4}$ alkylmercapto)benzoyl, cyanobenzoyl, dimethylaminobenzoyl, thiophenecarbonyl or furancarbonyl, or a pharmaceutically acceptable salt thereof, to a patient having melanoma, breast cancer, lung cancer or prostate cancer.

3. A method according to claim 1 for inhibiting the formation of tumor metastases which comprises administering an amount, which is safe and sufficient to inhibit the formation of tumor metastases, of a castanospermine ester of the formula:

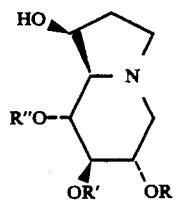

wherein R, R' and R" are selected so that two of them are hydrogen and the third is acetyl, propionyl, benzoyl, methylbenzoyl or furancarbonyl, or a pharmaceutically acceptable salt thereof, to a patient having melanoma, breast cancer, lung cancer or prostate cancer.

4. A method according to claim 1 wherein the patient has melanoma or lung cancer.

5. A method according to claim 1 wherein the patient has melanoma.

6. A method according to claim 1 for inhibiting the formation of tumor metastases which comprises administering an amount, which is safe and sufficient to inhibit the formation of tumor metastases, of a castanospermine ester of the formula:

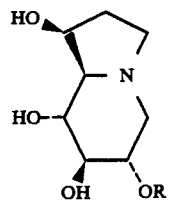

wherein R is alkanoyl of 1 to 18 carbon atoms, benzoyl, methylbenzoyl, methoxybenzoyl or furancarbonyl, or a pharmaceutically acceptable salt thereof, to a patient having melanoma, breast cancer, lung cancer or prostate cancer.

7. A method according to claim 6 wherein the patient has melanoma or lung cancer.

8. A method according to claim 6 wherein the patient has melanoma.

9. A method according to claim 1 wherein the daily dosage of compound administered is from about 0.1 to about 2,000 mg/kg body weight.

10. A method according to claim 9, wherein the daily dosage administered is from 1 to about 200 mg/kg body weight.

* * * * *